(12) United States Patent
Lehavi

(10) Patent No.: US 7,103,983 B2
(45) Date of Patent: Sep. 12, 2006

(54) MULTIPLE COMPONENT AND INTERACTIVE GROWTH CHART AND METHOD

(76) Inventor: Tali Lehavi, 13370 N. 91 St., Scottsdale, AZ (US) 85260

(*) Notice: Subject to any disclaimer, the term of this patent is extended or adjusted under 35 U.S.C. 154(b) by 0 days.

(21) Appl. No.: 10/889,752

(22) Filed: Jul. 13, 2004

(65) Prior Publication Data

US 2006/0010707 A1   Jan. 19, 2006

(51) Int. Cl.
*A61B 5/103* (2006.01)
*A63H 33/08* (2006.01)

(52) U.S. Cl. .................... 33/512; 33/679.1; 33/493; 446/124

(58) Field of Classification Search .............. 33/458, 33/478, 493, 494, 511, 512, 679.1, 832, 833; 434/187, 96, 406; 273/153 R, 275, 276, 273/289, 290; 428/33; 446/85, 108, 124, 446/125
See application file for complete search history.

(56) References Cited

U.S. PATENT DOCUMENTS

| | | | | |
|---|---|---|---|---|
| 887,994 | A * | 5/1908 | Bartram ..................... 33/833 |
| 1,198,263 | A * | 9/1916 | Pajeau ........................ 446/125 |
| 1,532,875 | A * | 4/1925 | Brown .................... 273/153 R |
| 2,197,031 | A * | 4/1940 | Davis ......................... 33/759 |
| 2,215,884 | A * | 9/1940 | Runge ......................... 33/512 |
| 2,324,334 | A * | 7/1943 | Sutton ......................... 33/512 |
| 2,410,696 | A * | 11/1946 | Wheeler ...................... 33/832 |
| D169,482 | S * | 5/1953 | Henke et al. ............... 446/125 |
| 2,895,753 | A * | 7/1959 | Fentiman .................... 446/125 |
| 3,415,007 | A * | 12/1968 | Howe ......................... 446/124 |
| 3,819,188 | A * | 6/1974 | Freedman ................... 446/124 |
| 4,041,611 | A * | 8/1977 | Dvorak ....................... 33/511 |
| 4,196,521 | A * | 4/1980 | Hutchinson et al. .......... 33/512 |
| 5,202,166 | A * | 4/1993 | Crompton et al. ........... 428/33 |
| 5,588,215 | A * | 12/1996 | Hart ............................ 33/494 |
| 6,003,235 | A * | 12/1999 | Chen .......................... 33/512 |
| 6,519,868 | B1* | 2/2003 | Pryor et al. ................. 33/832 |
| 6,599,045 | B1* | 7/2003 | Kolb ........................... 33/512 |
| 2004/0111909 | A1* | 6/2004 | Pourmanafzadeh ......... 33/512 |
| 2004/0154175 | A1* | 8/2004 | Shapiro ....................... 33/458 |
| 2005/0106989 | A1* | 5/2005 | Rincover ..................... 446/85 |

FOREIGN PATENT DOCUMENTS

DE          3626855 A1 *   2/1988
WO     WO93/04749 A1 *   3/1993

* cited by examiner

*Primary Examiner*—G. Bradley Bennett
(74) *Attorney, Agent, or Firm*—Jeffrey Weiss; Harry M. Weiss; Weiss & Moy, P.C.

(57) ABSTRACT

A multiple component, interactive growth chart assembled from a plurality of growth chart components. The individual components are preferably building block type, and have means for coupling one component on top of another. The components have a disclosed height, so that a user can calculate the height of a person who is positioned proximate a chart comprised of a plurality of assembled components. Preferably, the components have a heart shape. In one embodiment, coupling means are provided to permit lateral and/or other coupling directions, in addition to straight north-south coupling, so as to provide greater play flexibility.

13 Claims, 4 Drawing Sheets

MULTIPLE COMPONENT AND INTERACTIVE GROWTH CHART AND METHOD

FIELD OF THE INVENTION

The present invention relates to growth charts and, more particularly, to a building-block type of growth chart potentially having other game uses.

BACKGROUND OF THE INVENTION

It is common for a parent to place a growth chart in the room of a young child. A typical prior art growth chart consists of a poster or other static display, having thereon an incremental measurement display. For example, the display may consist of a series of hash marks, spread one inch apart, and typically includes labeling information to indicate the height corresponding to marks. Thus, the height of a child can be determined by having the child stand next to the chart, looking to see the highest hash mark which the top of the child's head reaches, and determining from the labeling information the height corresponding to that mark.

A limitation associated with prior art growth chart relates to their static nature. They are not adapted to be used by a child in the play of an interactive game, and generally have a single dedicated use as a chart. They also do not provide a child with a three-dimensional, building block type of appreciation of growth.

A need therefore exists for a growth chart that is interactive rather than static, that is building block type, and that may be used by a child for play purposes. The present invention satisfies this need and provides other, related, advantages.

SUMMARY OF THE INVENTION

In accordance with one embodiment of the present invention, a growth chart is disclosed. The growth chart comprises, in combination: a plurality of growth chart components adapted to be assembled together so as to measure the height of a person; wherein the plurality of growth chart components have a height; and means for disclosing the height to a user.

In accordance with another embodiment of the present invention, a method for measuring the height of a person is disclosed. The method comprises the steps of: providing a plurality of growth chart components adapted to be assembled together so as to measure the height of a person; wherein the plurality of growth chart components have a height; providing means for disclosing the height to a user; assembling a plurality of the growth chart components together; placing the person proximate the assembled growth chart components; determining a location of a top of the person's head relative to the assembled growth chart components; and computing a height of the location.

DETAILED DESCRIPTION OF THE PREFERRED EMBODIMENTS

Figure 1:
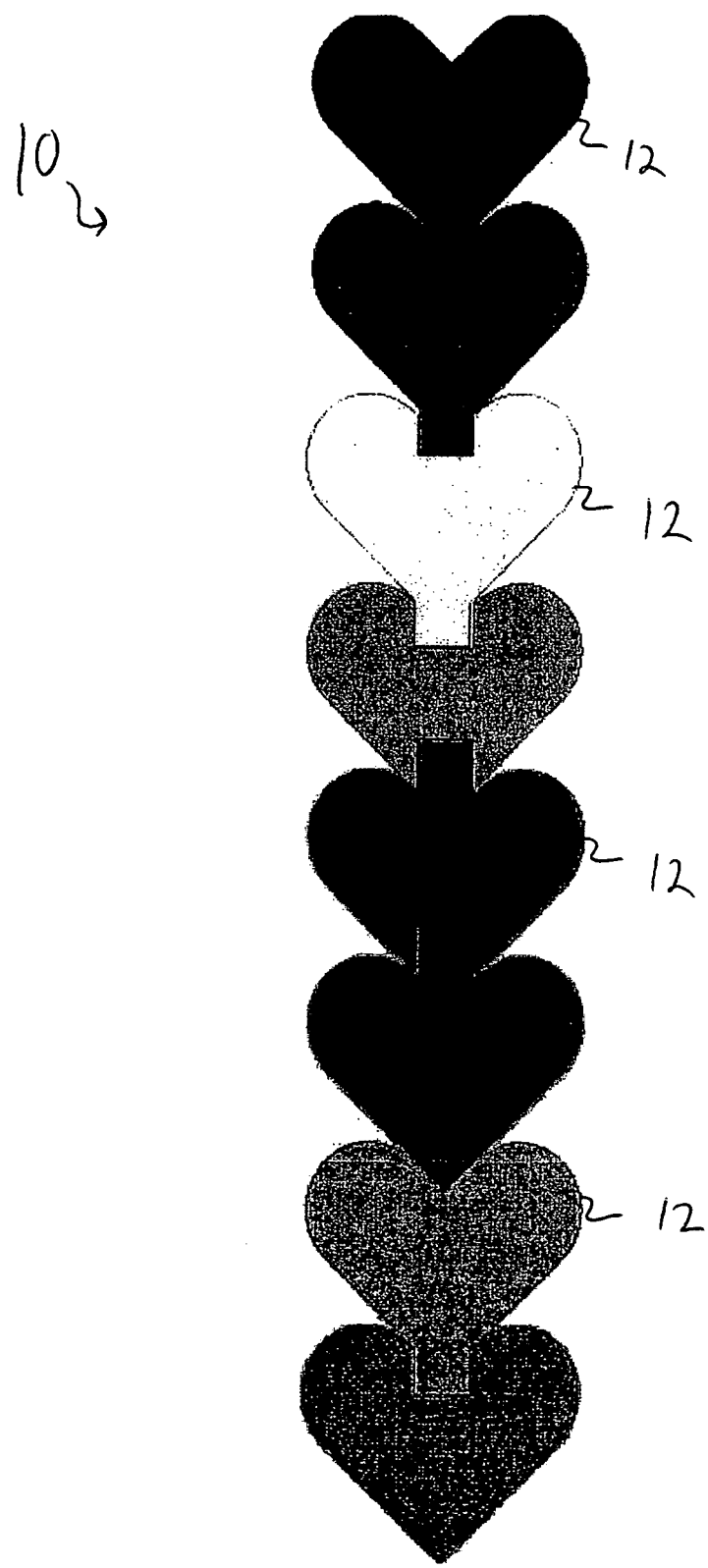
FIG. 1 is a front view of an interactive, component type of growth chart consistent with an embodiment of the present invention.

The present invention is directed to a multiple component, interactive type of growth chart comprised of individual chart components. Referring first to FIG. 1, a growth chart 10 is shown, formed of a plurality of stacked, coupled growth chart components 12. In this embodiment, the individual chart components 12 are heart-shaped, wherein the bottom of one component is coupleable to the top of a second component, so that one component can be securely stacked on top of another. (It should be noted that the heart shape represents only one possible configuration for a component 12. Certainly, other shapes may be provided, including for example blocks, body parts, bones, animated figures, etc.)

Figure 2:
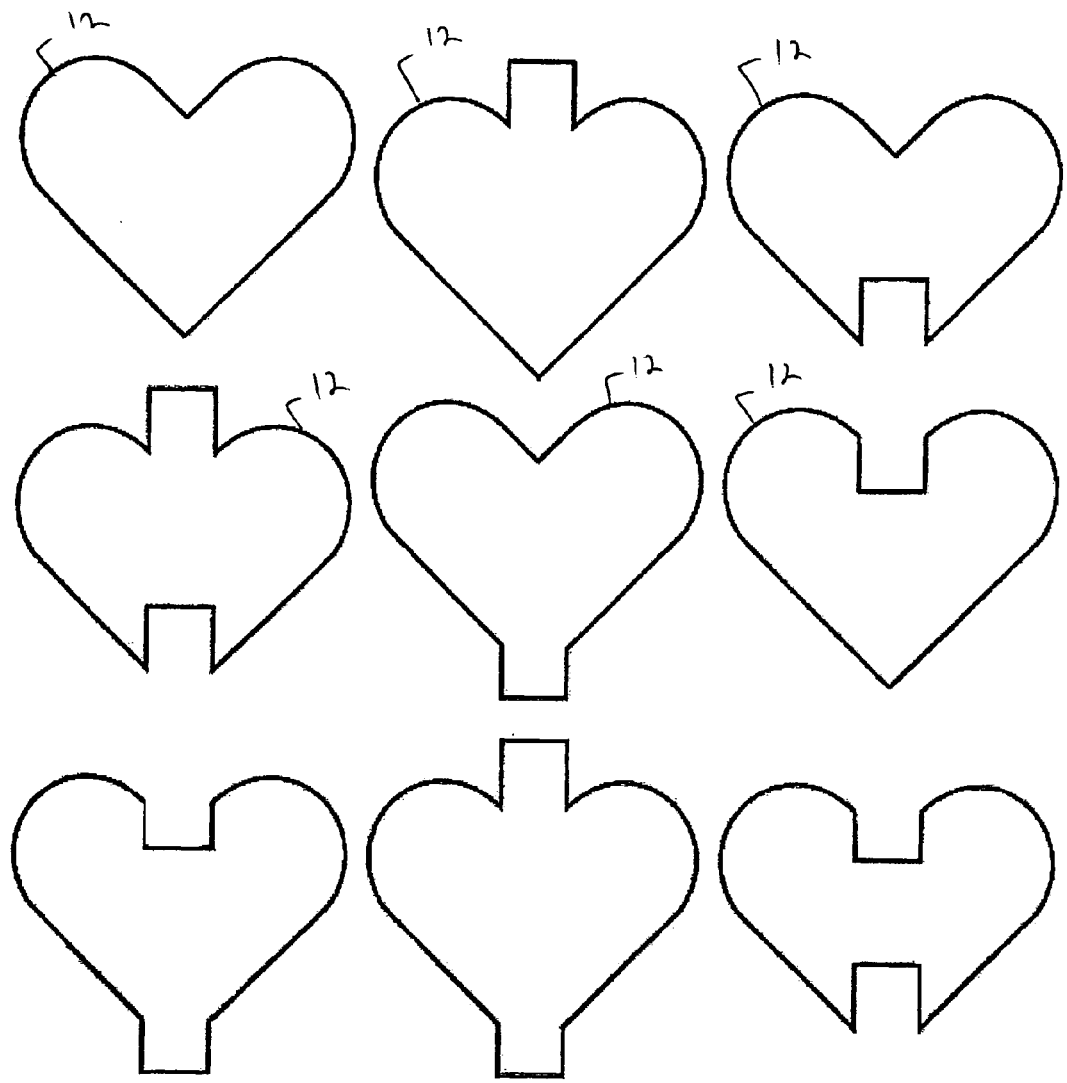
FIG. 2 is a front view of individual growth chart components consistent with an embodiment of the present invention.

Referring to FIGS. 1–2, coupling may be provided by providing corresponding male/female coupling areas on the components 12, which may be press-fit together in a substantially LEGO® building block style. As shown in these figures, components 12 can have a male top and a female bottom, a female top and a male bottom, a male top and a male bottom, or a female top and a female bottom. It may additionally be desired, for example for a component 12 that is to be positioned at the top of the chart 10, to provide a component 12 having a coupling area only on one end thereof. Of course, other coupling means could be utilized, such as VELCRO® hook and look tape, glue (particularly if the growth chart 10 is to become a permanent structure), snaps, interlocking and/or complementary structures on neighboring components 12, magnets, etc. (It may be desired to provide a power source and to provide for the transmission of a sound, light or other effect via one or more components 12.)

In one embodiment, individual components 12 are identically sized, and have a height that is disclosed to the user through labeling (for example, on the component 12, in packaging therefore or instructions provided therewith) or otherwise. For example, each component 12 may have a total height of one inch, two inches, five centimeters, etc. It may be further desired to display on the surface of a component 12, through hash marks, raised areas, or otherwise, indications of heights that are less than the total of the component 12. For example, if the component 12 is two inches high, it may be desired to provide hash marks at one inch, half inch, and/or other intervals.

In another embodiment, not all components 12 are identically sized or shaped. For example, it may be desired to provide a component 12 that is head-shaped, and for example that has the head of a popular animated or other character. (It may instead be desired to provide a component 12 that has the same shape as other components 12, for example that is also heart-shaped, but that has a face thereon to signify that it is the head of the chart 10.) That particular component 12 would preferably be positioned at the top of the growth chart 10, and would be temporarily removed for the addition of non-head shaped components 12 therebelow.

Figure 3:
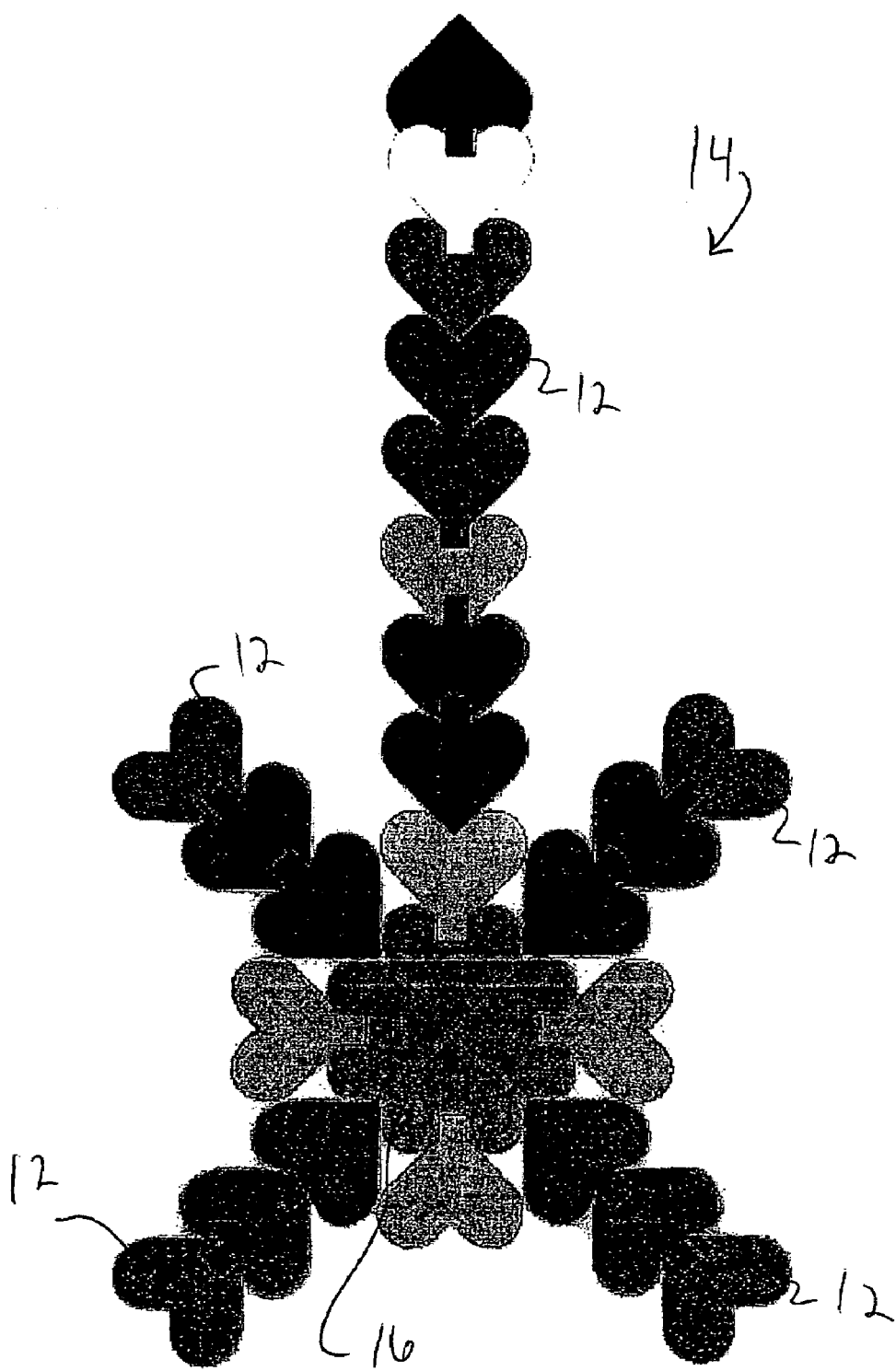
FIG. 3 is a front view of a multi-directional building structure constructed using growth chart components, consistent with an embodiment of the present invention.
Figure 4:
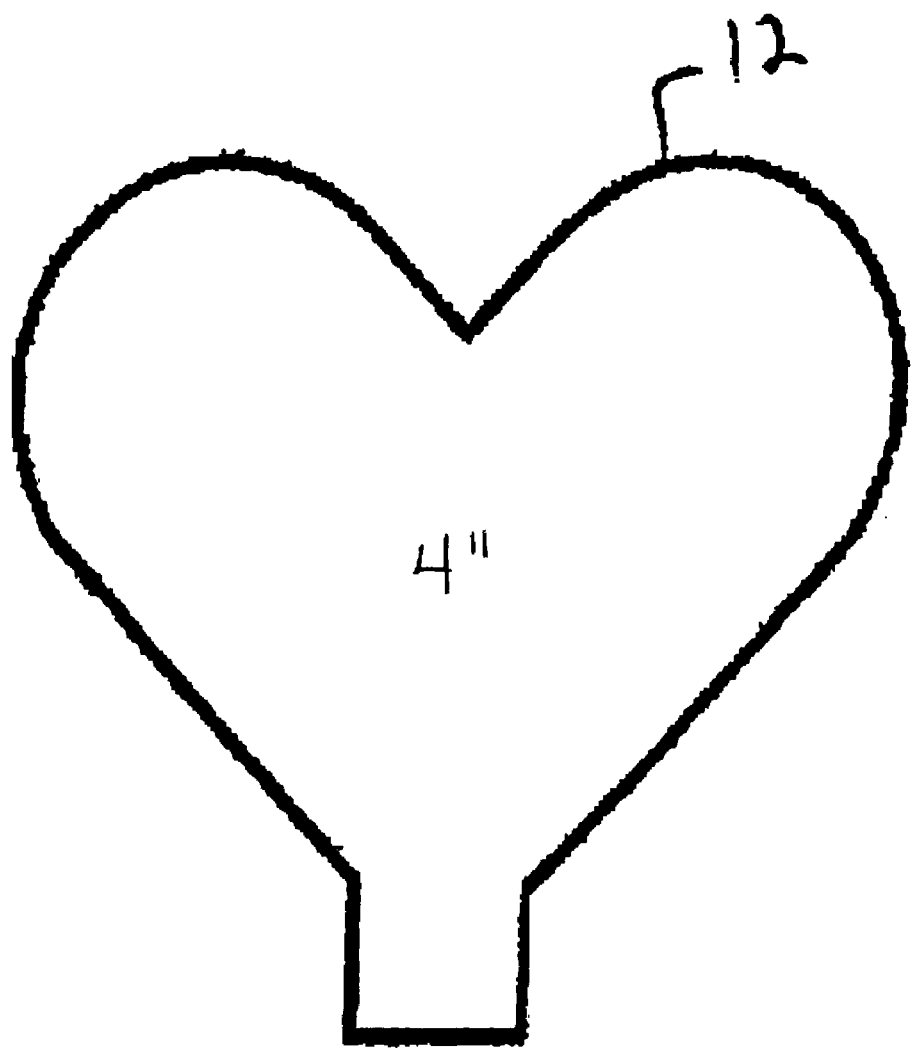
FIG. 4 is a front view of an individual growth chart component, illustrating indications of height marked on a surface thereof.

When not being used as a growth chart 10, the components 12 may be used for building block type of play. Referring now to FIG. 3, the use of components 12 to create a building block structure 14 is illustrated. It can be seen, in this embodiment, that it may be desired to provide a multi-axis coupling member 16, or to provide coupling means on surfaces other than the top and bottom of components 12 (not shown), to facilitate a broader variety of structural configurations. In this manner, in addition to being able to create structures following a north-south axis, it would be further possible to create structures that project laterally (for example to create arms) or in other directions as well.

Preferably, the components 12 are formed from molded plastic. However, they may be formed from other materials as well, including for example wood or felt. It may be desired to provide components 12 that may be marked by a user, so that particular heights/dates can be recorded. This would be particularly beneficial if the growth chart 10 is going to be more or less permanently assembled.

In this regard, it should be further noted that, in a preferred embodiment, the components 12 are three-dimensional. However, it may be desired to provide components 12 that are two-dimensional, and that consist for example of interlocking paper-type units that may be fitted together, on a wall, to form a chart 10 that can be increased in size as the person grows. Indeed, it may be desired to provide a software program permitting a user to customize components 12 by selecting shape, color, size and/or other design elements, and outputting the components 12 utilizing a printer.

In a preferred embodiment, the growth chart 10 is utilized to measure the height of a person. However, it may be utilized to measure other objects as well, including a doll, a pet, etc.

While the invention has been particularly shown and described with reference to preferred embodiments thereof, it will be understood by those skilled in the art that the foregoing and other changes in form and details may be made therein without departing from the spirit and scope of the invention.

The invention claimed is:

1. A growth chart comprising, in combination:
   a plurality of individual growth chart components adapted to be assembled together;
   wherein said plurality of individual growth chart components have a height and indications of height marked on a surface thereof; and
   a multi-axis coupling member to provide a common connection point for at least three individual growth chart components.

2. The growth chart of claim 1 wherein said individual growth chart components have means for coupling a bottom of one said individual growth chart component to a top of another said individual growth chart component.

3. The growth chart of claim 1 wherein said individual growth chart components are heart shaped.

4. The growth chart of claim 2 wherein said individual growth chart components are heart shaped.

5. The growth chart of claim 1 further comprising means for permitting lateral coupling of said individual growth chart components.

6. A method for interactively measuring the height of an object comprising the steps of:
   providing a plurality of individual growth chart components adapted to be assembled together;
   wherein said plurality of individual growth chart components have a height and indications of height marked on a surface thereof;
   assembling said plurality of said individual growth chart components together;
   coupling at least three individual growth chart components to a multi-axis coupling member;
   placing said object proximate said assembled growth chart components;
   determining a location of a top of said object relative to said indications of height on the surface of said assembled growth chart components to measure the height of said object; and
   computing a height of said location.

7. The method of claim 6 wherein said individual growth chart components have means for coupling a bottom of one said individual growth chart component to a top of another said growth chart component.

8. The method of claim 6 wherein said individual growth chart components are heart shaped.

9. The method of claim 7 wherein said individual growth chart components are heart shaped.

10. The method of claim 6 further comprising means for permitting lateral coupling of said individual growth chart components.

11. The method of claim 6 wherein said object is a person.

12. The method of claim 6 wherein said object is a doll.

13. The method of claim 6 wherein said object is a pet.

* * * * *